United States Patent [19]

Simon et al.

[11] 4,287,206
[45] Sep. 1, 1981

[54] HALOGEN DERIVATIVES OF 8-HYDROXYCARBOXYLIC ACIDS; THE PROCESSES FOR THEIR PREPARATION AND MEDICAMENTS IN WHICH THEY ARE PRESENT

[75] Inventors: Pierre Simon, Sevres; Jacques Dreux, Lyons, both of France

[73] Assignee: Laboratoires Hoechst, S.A., Puteaux, France

[21] Appl. No.: 72,411

[22] Filed: Sep. 4, 1979

[30] Foreign Application Priority Data

Sep. 5, 1978 [FR] France ............................... 78 25457

[51] Int. Cl.³ ................. A61K 31/335; C07D 309/30; C07C 59/11
[52] U.S. Cl. ................................ 424/279; 260/343.5; 260/465 D; 562/470; 424/317
[58] Field of Search ..................... 260/343.5; 562/470; 424/279, 317

[56] References Cited

U.S. PATENT DOCUMENTS

| | | | |
|---|---|---|---|
| 4,113,742 | 9/1978 | Simon ................................. | 260/343.5 |
| 4,163,799 | 8/1979 | Simon ................................. | 424/317 |
| 4,198,425 | 4/1980 | Mitsui et al. .................. | 260/343.5 X |

FOREIGN PATENT DOCUMENTS

| | | | |
|---|---|---|---|
| 643891 | 8/1964 | Belgium ............................... | 260/343.5 |
| 315583 | 10/1956 | Switzerland ........................... | 260/343.5 |

Primary Examiner—Ethel G. Love
Attorney, Agent, or Firm—Curtis, Morris & Safford

[57] ABSTRACT

Halogen derivatives of 8-hydroxycarboxylic acids, which correspond to the formula

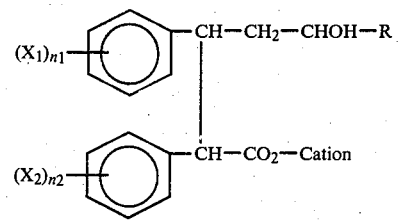

(open form, in a basic medium) or to the formula

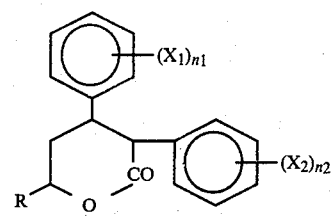

(cyclized form, in an acid medium) in which formulae: $X_1$ and $X_2$ are halogen atoms, $n_1$ and $n_2$ are integers between 0 and 5, but, if $n_1=0$, $n_2$ is different from 0, and vice versa, R is a hydrogen atom or an alkyl or aryl group, and Cation represents an ion originating from a base, or a metal ion, which is pharmaceutically compatible are suitable as antidepressants having a psychostimulant action.

6 Claims, 1 Drawing Figure

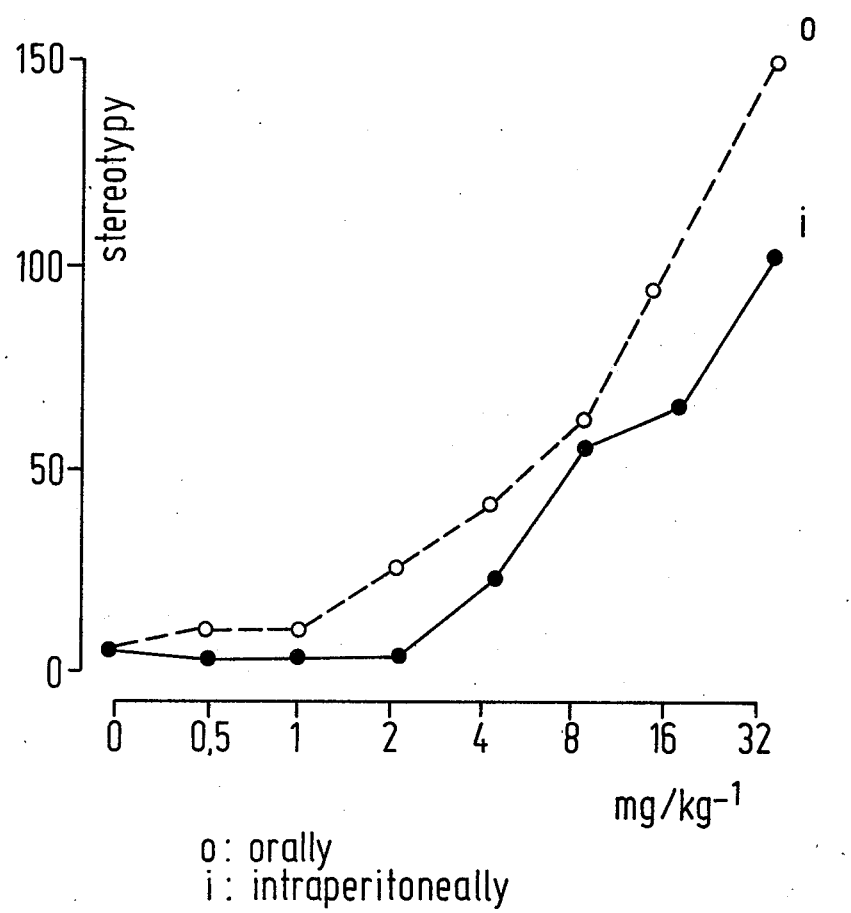

HALOGEN DERIVATIVES OF δ-HYDROXYCARBOXYLIC ACIDS; THE PROCESSES FOR THEIR PREPARATION AND MEDICAMENTS IN WHICH THEY ARE PRESENT

The present invention relates to new halogen derivatives of δ-hydroxycarboxylic acids, to the processes for their preparation and to new medicaments in which these derivatives are present.

The research work carried out in the field of α-pyrone derivatives, has enabled to demonstrate, in particular, that 6-methyl-3,4-diphenyl-3,4,5,6-tetrahydropyrone-2 of the formula I below:

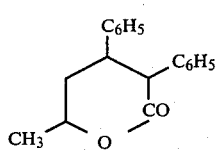

and the salts of 5-hydroxy-2,3-diphenylhexanoic acid, of the formula II below:

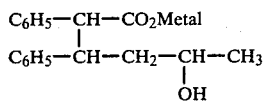

are therapeutic products possessing psychotropic properties and more particularly psychostimulant properties (compare French Pat. Nos. 2,277,579, 2,314,186 and 2,373,281).

By pursuing the above work, the Inventors have now succeeded in demonstrating that certain halogen derivatives of δ-hydroxycarboxylic acids (with an open or cyclized chain) constitute psychostimulant medicaments having an antidepressive action. Although certain substances of this important family exhibit, from the pharmacological point of view, a sedative-type spectrum of properties with reduction of the motor activity, other substances, on the other hand, by virtue of their stimulant antidepressive action, have made it possible to achieve very considerable progress in the treatment of depression.

The present invention relates to new halogen derivatives of δ-hydroxycarboxylic acids, which correspond to the general formula (IIIa) below:

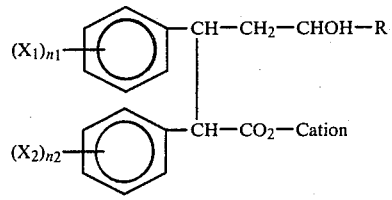

(open form, in a basic medium) or to the general formula IIIb below:

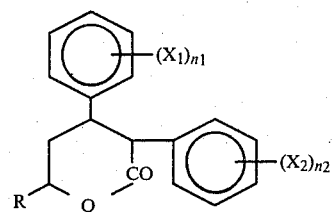

(cyclized form, in an acid medium) in which formulae: $X_1$ and $X_2$ are halogen atoms, $n_1$ and $n_2$ are integers between 0 and 5, with the proviso, however, that if $n_1=0$, $n_2$ is different from 0, and vice versa, R is a hydrogen atom or an alkyl or aryl group, and Cation represents an ion originating from a base, or a metal ion, which is pharmaceutically compatible.

The present invention also relates to a process for the preparation of derivatives of the general formulae IIIa and IIIb, which comprises preparing a halogenoketonitrile in a first step and then converting it, by hydrolysis and reduction, into the corresponding compound of the general formula III, which compound is in the open form (a) in a basic medium or in the cyclized form (b) in an acid medium.

According to an advantageous embodiment of the process forming the subject of the present invention, the halogenoketonitrile is first reduced to give the corresponding halogenohydroxynitrile and the latter is then cyclized and hydrolyzed in the presence of an acid to give the compound of the general formula IIIb.

According to another embodiment of the process forming the subject of the present invention, the ketonitrile is first converted into the corresponding halogenoketoacid by hydrolysis in the presence of acid, and the halogenoketoacid is then reduced and cyclized to give a compound of the general formula IIIb.

According to another advantageous embodiment of the process forming the subject of the invention, the halogenoketonitrile is first converted into the ketoacid by acid hydrolysis, the ketoacid is then converted into the keto-salt by means of a pharmaceutically compatible base, and the keto-salt is then reduced to give a compound of the general formula IIIa.

According to a further advantageous embodiment of the process forming the subject of the invention, the halogenoketonitrile is converted into the ketoester by acid treatment in the presence of an alcohol, the ketoester is then reduced to give the corresponding hydroxyester and, finally, the hydroxyester is hydrolyzed by means of a pharmaceutically compatible base to give a compound of the general formula IIIa.

According to an advantageous variant of this embodiment, the ketoester is first treated with a pharmaceutically compatible base to give a keto-salt and the keto-salt is then reduced to give a compound of the general formula IIIa.

According to a further advantageous embodiment of the process forming the subject of the present invention, the halogenoketonitrile is converted into the corresponding keto-salt by alkaline hydrolysis, and the keto-salt is then reduced.

According to another advantageous embodiment of the process forming the subject of the present invention, the halogenoketonitrile is prepared by reacting an α-ethylenic ketone, which corresponds to the general formula IV below:

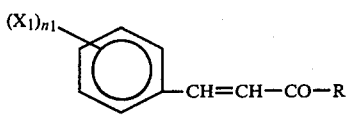

(IV)

with benzyl cyanide of the general formula V below:

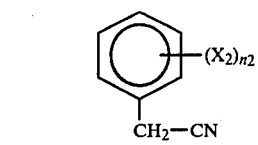

(V)

to give a compound of the general formula VI below:

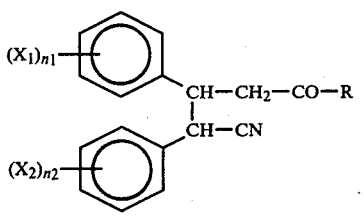

(VI)

in which formulae: $X_1$, $X_2$, $n_1$, $n_2$ and R have the same meaning as above.

According to a particularly advantageous embodiment of the process forming the subject of the present invention, during each synthesis step, several recrystallizations are carried out in suitable solvents in order to separate the trans (threo) derivatives from the cis (erythro) derivatives or to enrich the mixture in one of these trans or cis derivatives.

By following this procedure, sucessfully separating out the various stereoisomers of these products has been accomplished, in particular the trans form:

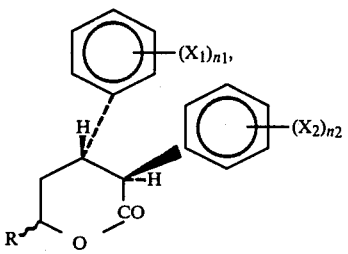

(A)

the cis form:

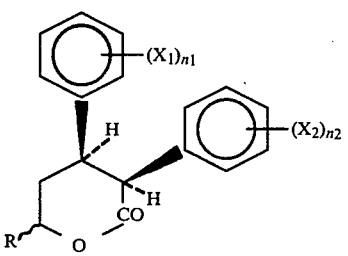

(B)

and also the two diastereoisomers, with respect to R, respectively corresponding to the above trans and cis forms, namely: the α form:

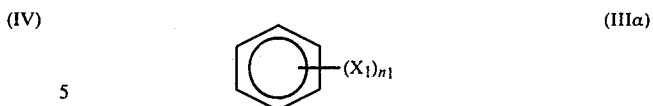

(IIIα)

and the β form:

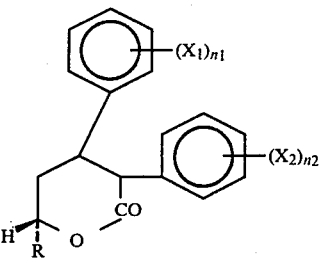

(IIIβ)

According to an advantageous embodiment of the process forming the subject of the present invention, the intermediates consisting of hydroxynitriles, ketonitriles, ketoacids and ketoesters, and also the pyrones, are recrystallized from polar solvents, the intermediates consisting of hydroxyesters are recrystallized from polar solvents which do not contain oxygen, and the keto-salts and the hydroxy-salts are recrystallized from polar solvents containing at least 10% of water.

According to another embodiment of the subject of the invention, the cyclization in an acid medium, to give the derivatives of the general formula (III), is carried out at ambient temperature if it is desired to obtain the diastereoisomer of the β form, or at the reflux temperature if it is desired to obtain the diastereoisomer of the α form.

According to another embodiment of the subject of the invention, the reduction of the keto-salts to give the corresponding hydroxy-salts is carried out using a solution of $NaBH_4$ in water.

In fact, it has been observed that the reduction system $NaBH_4$/ethyl alcohol can act as an epimerizing agent since, if the keto-salts are reduced with $NaBH_4$ in an aqueous medium, it is the virtually pure cis isomer, and not the mixture, which is obtained.

The present invention relates to halogen derivatives of δ-hydroxycarboxylic acids, of the general formulae IIIa and IIIb, and also to their stereochemically pure forms of the formulae (A), (B), IIIα and IIIβ.

The present invention further relates to medicaments which contain, or consist of, a mixture of the said derivatives of the formulae IIIa and IIIb.

Apart from the above variants, the invention also includes other variants which will become apparent from the description which now follows.

The present invention more particularly includes the new medicaments which consist of, or comprise, the halogen derivatives of δ-hydroxycarboxylic acids, according to the above variants, and also the various Galenic forms of administration of these medicaments.

The invention will be more clearly understood with the aid of the following additional descriptive text, which refers to examples of the preparation of the compounds according to the present invention, and also to an account of pharmacological and pharmacodynamic experiments using these compounds, which very clearly demonstrate the effectiveness of the new medicaments according to the present invention as antidepressants having a psychostimulant action.

However, it must be clearly understood that the preparation examples which will be described below, and also the account of pharmacological and pharmacodynamic experiments, are given solely by way of an illustration of the subject of the invention and in no way constitute a limitation thereof.

EXAMPLE I

Preparation of Trans-4-(4'-chlorophenyl)-6-methyl-3-phenyl-3,4,5,6-tetrahydropyrone-2

(a) Preparation of erythro-2-(4'-chlorophenyl)-4-oxo-1-phenylpentanecarbonitrile

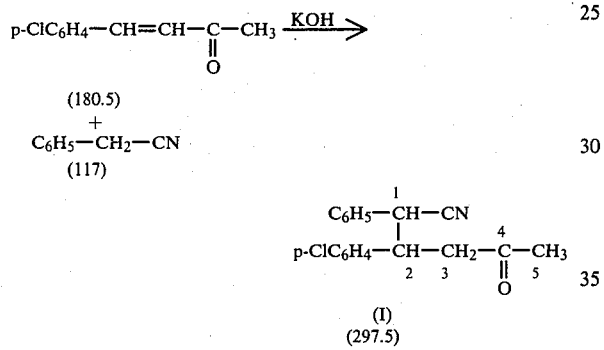

78 g (0.43 mole) of 1-(4'-chlorophenyl)-but-1-en-3-one, 50.5 g (0.43 mole) of benzyl cyanide and 170 cm³ of a hexane/absolute alcohol mixture (30/70) are placed in a 250 cm³ reactor equipped with a magnetic stirrer. The contents of the reactor are cooled to 0° C. with an ice/salt mixture, and the catalyst (10 cm³ of 2 N ethanolic potassium hydroxide solution) is then added in the course of 10 minutes. The temperature of the reaction medium during the addition of the catalyst is about 5° C.

The precipitation of the reaction product develops about 20 minutes after the addition of the catalyst is complete. One hour after the start of the precipitation, it is no longer possible to stir the reaction medium and the reactor is then placed in a refrigerator for about 12 hours.

The contents of the reactor are filtered and the product is washed with 100 cm³ of cold hexane in order to remove the unreacted reactants, and then with 100 cm³ of cold methanol in order to remove the potassium hydroxide. After drying in vacuo, 115.5 g of whitish crystals of the ketonitrile (I), melting point = 125°–128° C. (Büchi apparatus), are isolated; yield = 90%. The product is recrystallised once from absolute alcohol. Melting point = 130°–132° C.; yield of the recrystallization: 90%.

| Analysis: | $C_{18}H_{16}ClNO$ | | C | H | Cl |
|---|---|---|---|---|---|
| (297.5) | | Calculated % | 72.61 | 5.41 | 11.90 |
| | | Found % | 72.66 | 5.51 | 11.78 |

| I.R. (KBr): | $\nu\ C\equiv N : 2{,}250\ cm^{-1}$; $\nu\ C=O : 1{,}710\ cm^{-1}$. |
|---|---|
| NMR: | $\delta$ : 6.85–7.40 ppm, signal for 9 aromatic protons. |
| (CDCl₃) | $\delta$ : 4.35 ppm, doublet for one proton $H_{(1)}$. $JH_{(1)}$–$H_{(2)}$ = 7Hz. |
| | $\delta$ : 3.65 ppm, multiplet for one proton $H_{(2)}$. |
| | $\delta$ : 3.10 ppm, multiplet for 2 protons $H_{(3)}$. |
| | $\delta$ : 2.20 ppm, singlet for 3 protons $CH_{3(5)}$ for one diastereoisomer. |
| | $\delta$ : 2.10 ppm, singlet for 3 protons $CH_{3(5)}$ for the other diastereoisomer at the carbons in the 1- and 2-positions, the percentage of which is less than 10%. The configuration of the predominant diastereoisomer is futhermore determined as being erythro. |

By continuing to recrystallize the resulting product from absolute alcohol until a constant melting point of 132° C. is reached, a single pure diastereoisomer of the erythro configuration is isolated.

(b) Preparation of trans-4-(4'-chlorophenyl)-6-methyl-3-phenyl-3,4,5,6-tetrahydropyrone-2

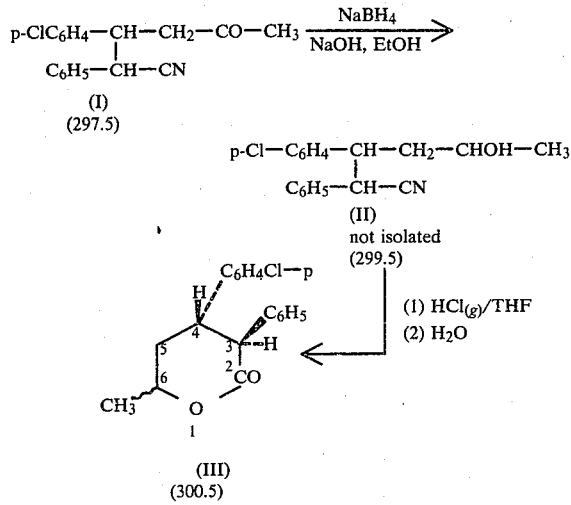

A suspension, in 500 cm³ of absolute alcohol, of 50 g (0.168 mole) of the ketonitrile (I) obtained above is placed in a one liter round-bottomed flask equipped with a magnetic stirrer. A solution of 3.2 g (0.084 mole) of sodium borohydride and 0.1 g of sodium hydroxide in 20 cm³ of water is then added dropwise (in the course of about 15 minutes) and the mixture is stirred at ambient temperature for 12 hours. The temperature of the reaction medium after the addition of the catalyst is about 30° C. and the solution becomes clear. The precipitation of the reaction products develops about 1 hour after the addition of the catalyst is complete, and the temperature of the reaction medium returns to ambient temperature.

The alcohol is then evaporated off in vacuo and the residue (nitrile-alcohol and inorganic salts) is taken up in 400 cm³ of methylene chloride. The inorganic salts are extracted with 100 cm³ of water, and the organic phase is washed with water until the washings are neutral, and dried over sodium sulfate. After evaporating off the solvent, 49.5 g of crude product (alcohol-nitrile) are obtained; yield = 98%.

In view of the fact that, by starting with a ketonitrile (I) of the erythro configuration, an alcohol-nitrile is obtained, the configuration of which is furthermore determined as being threo, it is acknowledged that epimerization takes place during the preparation of the alcohol-nitrile.

The product obtained is taken up in 120 cm³ of anhydrous tetrahydrofuran (THF). Dry hydrogen chloride gas is bubbled into this solution until saturation is reached, the temperature of the medium being kept at about 0° C. After standing for 12 hours at low temperature (−10° C.), the hydrochloric acid is removed by a stream of air and the THF is evaporated off. The residue is heated under reflux in 100 cm³ of water for 1 hour. After cooling, the organic phase is taken up in 100 cm³ of methylene chloride, and the aqueous phase is extracted with the same solvent (2×50 cm³). The organic phases are combined and washed with water and then with a solution of sodium bicarbonate, and they are finally washed with water until the washings are neutral. The organic solution is dried over sodium sulfate. After evaporating off the solvent, the crude pyrone is recrystallized from 100 cm³ of absolute alcohol. 30 g of pyrone (III) are isolated. Melting point=139°-141° C. Yield=60%.

| Analysis: | $C_{18}H_{17}ClO_2$ | | C | H | Cl |
|---|---|---|---|---|---|
| | (300.5) | Calculated % | 71.88 | 5.70 | 11.79 |
| | | Found % | 71.67 | 5.59 | 11.81 |
| I.R. (KBr): | $\nu\ C{=}O : 1{,}730\ cm^{-1}$. | | | | |
| NMR: | | | | | |
| $(CD_3{-}CO{-}CD_3)$ | $\delta$ : 7.15 ppm, signal for 9 aromatic protons. | | | | |
| | $\delta$ : 5.00 ppm, multiplet for $H_{(6)}$. | | | | |
| | $\delta$ : 4.20 ppm, doublet for $H_{(3)}$. J $H_{(3)}$-$H_{(4)}$ = 11.4 Hz. | | | | |
| | $\delta$ : 3.90 ppm, doublet for $H_{(3)}$. J $H_{(3)}$-$H_{(4)}$ = 11.8 Hz for the other isomer. | | | | |
| | $\delta$ : 3.60 ppm, multiplet for $H_{(4)}$. | | | | |
| | $\delta$ : 2.15 ppm, multiplet for the two protons $H_{(5)}$ of the two isomers. | | | | |
| | $\delta$ : 1.45 ppm, doublet for 3 protons $CH_{3(6)}$. J $CH_3$-$H_{(6)}$ = 6 Hz. | | | | |
| | $\delta$ : 1.40 ppm, doublet for 3 protons $CH_{3(6)}$ for the other isomer. J $CH_3$-$H_{(6)}$ = 6 Hz. | | | | |

The percentage of the two isomers is 50% (measured from the signals of the methyls in the 6-position). The coupling constant between the protons in the 3- and 4-positions, namely 11.4 and 11.8 Hz, indicates an axial trans conformation for the protons $H_{(3)}$ and $H_{(4)}$, and the two substituents in the 3- and 4-positions are therefore in the equatorial trans position.

Mass Spectrum: Two molecular peaks at 300 ($Cl^{35}$) and 302 ($Cl^{37}$).

EXAMPLE II

Preparation of Threo-2-(4'-chlorophenyl)-4-hydroxy-1-phenylpentanecarbonitrile, IIα

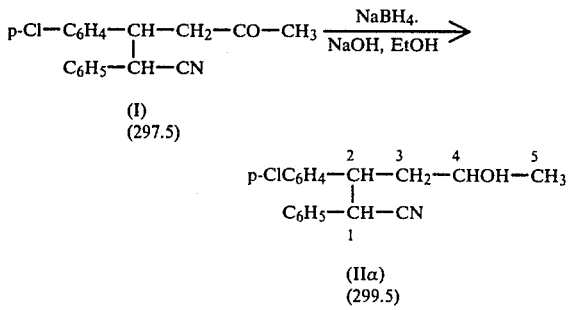

A suspension, in 400 cm³ of absolute alcohol, of 40 g (0.134 mole) of the ketonitrile (I) obtained as indicated in Example I, melting point=130°-132° C., is placed in a one liter round-bottomed flask equipped with a magnetic stirrer. A solution of 2.55 g (0.067 mole) of sodium borohydride and 0.1 g of sodium hydroxide in 20 cm³ of water is then added dropwise (in the course of about 15 minutes) and the mixture is stirred at ambient temperature for 12 hours. The temperature of the reaction mixture after the addition of the catalyst is about 30° C. and the solution becomes clear. The precipitation of the reaction products develops about 1 hour after the addition of the catalyst is complete, and the temperature of the reaction medium returns to ambient temperature.

The alcohol is then evaporated off in vacuo and the residue (nitrile-alcohol and inorganic salts) is taken up in 400 cm³ of methylene chloride. The inorganic salts are extracted with 100 cm³ of water, and the organic phase is washed with water until the washings are neutral, and dried over sodium sulfate. After evaporating off the solvent, 39.5 g of crude product (alcohol-nitrile) are obtained; yield: 98%.

The crude product, which is an equimolecular mixture of two diastereoisomers (IIα) and (IIβ), with respect to the carbon in the 4-position, is recrystallized twice from 100 cm³ of ethyl alcohol of 95° (Gay Lussac) strength. The threo isomer (IIα), melting point=169°-170° C., is isolated. Yield of the recrystallization: 75%, calculated by taking into account the fact that the product obtained comprises two threo diastereoisomers, differing in the configuration of CHOH at the carbon in the 4-position, and that the object of this preparation is to isolate only one of these isomers (IIα) in order to give the trans-pyrone or (IIIα) (see Example III below).

The filtrate from the first recrystallization of (IIα) must be kept because it contains the diastereoisomer (IIβ) which will subsequently be used to prepare the pyrone (IIIβ) (compare Example IV).

In view of the fact that, by starting with a ketonitrile (I) of the erythro configuration, two pyrones (IIIα) and (IIIβ) of the trans configuration are obtained, it is acknowledged that epimerization takes place during the preparation of the alcohol-nitrile. The configuration of the product obtained (IIα) is furthermore determined as being threo.

| Analysis: | $C_{18}H_{18}ClNO$ | | C | H | Cl |
|---|---|---|---|---|---|
| (IIα) | (299.5) | Calculated % | 72.24 | 6.02 | 11.70 |
| | | Found % | 72.17 | 6.07 | 11.64 |
| I.R. (KBr): | $\nu\ C{\equiv}N : 2{,}250\ cm^{-1}$, $\nu\ O{-}H : 3{,}525\ cm^{-1}$. | | | | |
| (IIα) | | | | | |
| NMR | $\delta$ : 6.80-7.30 ppm, signal for 9 aromatic protons. | | | | |
| $(CDCl_3)$ | $\delta$ : 4.15 ppm, doublet for one proton $H_{(1)}$. J $H_{(1)}$-$H_{(2)}$ = 6 Hz. | | | | |
| (IIα) | $\delta$ : 3.80 ppm, multiplet for one proton $H_{(2)}$. | | | | |
| | $\delta$ : 3.20 ppm, multiplet for one proton $H_{(4)}$. | | | | |
| | $\delta$ : 1.95 ppm, two superimposed triplets for the two protons $CH_{2(3)}$. J $CH_{2(3)}$-$H_{(2)}$ = J $CH_{2(3)}$-$H_{(4)}$ = 6 Hz. | | | | |
| | $\delta$ : 1.15 ppm, doublet for 3 protons $CH_{3(5)}$. J $CH_3$-$H_{(4)}$ = 6 Hz. | | | | |

EXAMPLE III

Preparation of
Trans-4-(4'-chlorophenyl)-6-methyl-3-phenyl-3,4,5,6-tetrahydropyrone-2, IIIα

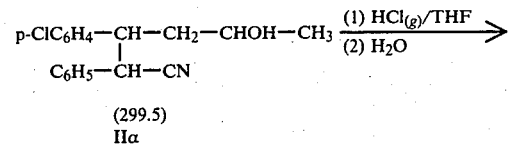

(299.5)
IIα

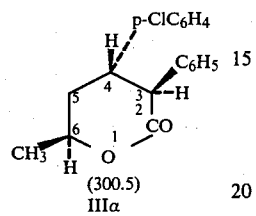

(300.5)
IIIα

The procedure described in Example I is used for preparing the pyrone. After evaporating off the solvent, the crude pyrone is recrystallized once from absolute alcohol. A single pure trans isomer of the pyrone is isolated.

Melting point = 136°–137° C.;
yield: 60%.

| I.R. (KBr): | $\nu$ C=O : 1,750 cm$^{-1}$. |
|---|---|
| NMR: | δ: 7.10 ppm, signal for 9 aromatic protons. |
| (CD$_3$COCD$_3$) | δ: 4.95 ppm, multiplet for H$_{(6)}$. |
| | δ: 4.15 ppm, doublet for H$_{(3)}$. J H$_{(3)}$-H$_{(4)}$ = 11.4 Hz. |
| | δ: 3.60 ppm, multiplet for H$_{(4)}$. |
| | δ: 2.20 ppm, multiplet for the two protons H$_{(5)}$. |
| | δ: 1.42 ppm, doublet for 3 protons CH$_{3(6)}$. J CH$_3$ − H$_{(6)}$ = 6 Hz. |

EXAMPLE IV

Preparation of
Trans-4-(4'-chlorophenyl)-6-methyl-3phenyl-3,4,5,6-tetrahydropyrone-2, IIIβ

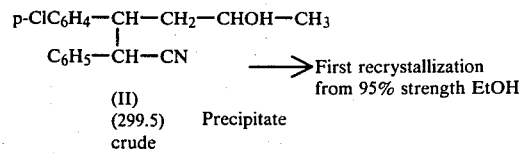

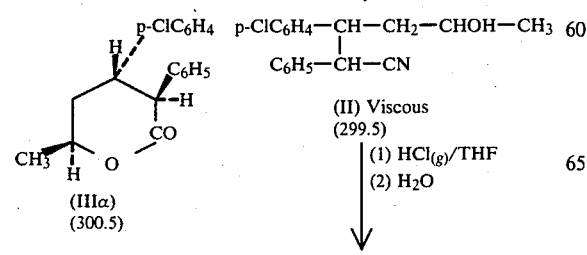

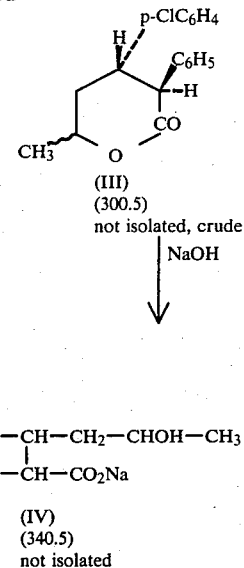

(III)
(300.5)
not isolated, crude

| NaOH (IIIβ)
(300.5)

←HCl  p-ClC$_6$H$_4$—CH—CH$_2$—CHOH—CH$_3$
            |
       C$_6$H$_5$—CH—CO$_2$Na (IV)
(340.5)
not isolated The procedure described in Example I is used to prepare the alcohol-nitrile. The crude product obtained is recrystallized once from alcohol of 95° (Gay Lussac) strength. The filtrate from this recrystallization is recovered and, by evaporating off the alcohol, a viscous alcohol-nitrile (II), which is rich in the βisomer (α: 25%, β: 75%), is obtained. This percentage was measured from the signals of the methyls in the 6-position, in the NMR spectrum of the pyrone (III) obtained from this alcohol-nitrile.

The preparation of the pyrone is continued by employing the same procedure as in Example I. A solution of 2.1 g (0.0528 mole, 5% excess) of sodium hydroxide in 45 cm$^3$ of water is added to 15 g (0.0501 mole) of crude pyrone (III) and the mixture is heated under reflux for one hour. After cooling, the aqueous solution is washed with methylene chloride in order to remove the unsaponifiable material, and the aqueous phase is acidified with a solution of HCl (10% strength). It is stirred at ambient temperature for one hour. The organic phase is taken up in 45 cm$^3$ of methylene chloride and the aqueous phase is extracted with the same solvent (2×20 cm$^3$). The organic phases are combined and washed with water and then with a solution of sodium bicarbonate, and they are finally washed with water until the washings are neutral. The organic solution is dried over sodium sulfate. After evaporating off the solvent, the crude pyrone (3.5 g, yield 31%) is recrystallized from absolute alcohol until a constant melting point is reached. A single pure trans isomer of the pyrone IIIβ is isolated.

Melting point = 159°–160° C. Overall yield of the operation, based on the viscous alcohol-nitrile (II): 16%.

| I.R. (KBr) | $\nu$ C=O: 1,725 cm$^{-1}$. |
|---|---|
| NMR | δ : 7.15 ppm, signal for 9 aromatic protons. |
| (CD$_3$COCD$_3$) | δ : 4.90 ppm, multiplet for H$_{(6)}$. |
| | δ : 3.95 ppm, doublet for H$_{(3)}$. J H$_{(3)}$-H$_{(4)}$ = 11.8 Hz. |
| | δ : 3.60 ppm, multiplet for H$_{(4)}$. |
| | δ : 2.20 ppm, multiplet for the two protons H$_{(5)}$. |
| | δ : 1.40 ppm, doublet for 3 protons CH$_{3(6)}$. |

-continued

J CH$_3$ — H$_{(6)}$ = 6 Hz.

EXAMPLE V

Separation of the Two Pure Isomers α and β of Trans-4-(4′-chlorophenyl)-6-methyl-3-phenyl-3,4,5,6-tetrahydropyrone-2

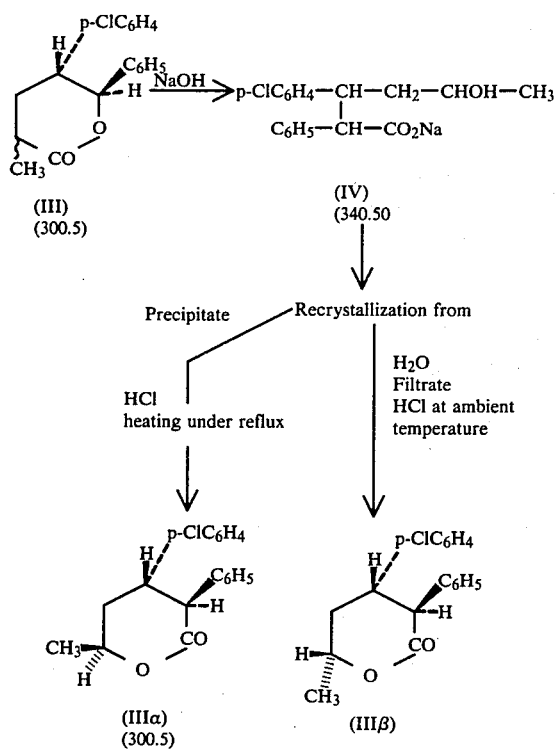

A solution of 0.28 g (0.0070 mole, 5% excess) of sodium hydroxide in 15 cm$^3$ of water is added to 2 g (0.0066 mole) of pyrone (III). After heating under reflux for 15 minutes, all the pyrone has dissolved and heating is then continued for 1 hours. On cooling, the contents of the round-bottomed flask solidify and are filtered on a glass frit. The filtrate (IVβ) (which contains the hydroxy-salt of the pyrone β) is kept and the precipitate (IVα) (hydroxy-salt of the pyrone α) is recrystallized from water.

Melting point=274° C. The pyrone (IIIα) is obtained by heating the recrystallized hydroxy-salt (IVα) under reflux, for 1 hour, with 5 cm$^3$ of a solution of hydrochloric acid in water (10% strength). After cooling, extraction is carried out with methylene chloride. The organic phase is washed with sodium bicarbonate and with water until the washings are neutral. After drying over sodium sulfate, the solvent is evaporated off. The crude pyrone recovered (0.300 g; yield: 30%) is recrystallized from absolute alcohol. 0.270 g of pyrone (IIIα) is obtained.

Melting point=136°-137° C.,
yield: 27%.

The pyrone (IIIβ) is obtained by acidifying the filtrate (IVβ) with a solution of hydrochloric acid (10% strength) and by stirring for one hour 15 minutes at ambient temperature. Extraction is carried out with methylene chloride and the organic phase is washed with sodium bicarbonate and with water until the washings are neutral. After drying over sodium sulfate, the methylene chloride is evaporated off. The crude pyrone recovered (0.600 g yield: 60%) is recrystallized from absolute alcohol. 0.520 g of pyrone (IIIβ) is obtained.

Melting point=159°-160° C.,
yield: 52%.

EXAMPLE VI

Preparation of Cis-4-(4′-chlorophenyl)-6-methyl-3-phenyl-3,4,5,6-tetrahydrophyrone-2, III (a) Preparation of erythro-2-(4′-chlorophenyl)-4-oxo-1-phenylpentanecarbonitrile

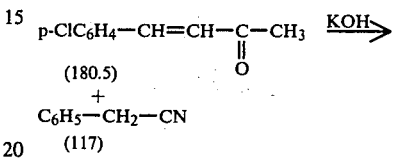

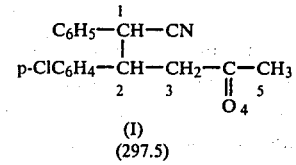

The method described in Example I is used for the preparation of this product.

(b) Preparation of erythro-3-(4′-chlorophenyl)-5-oxo-2-phenylhexanoic acid

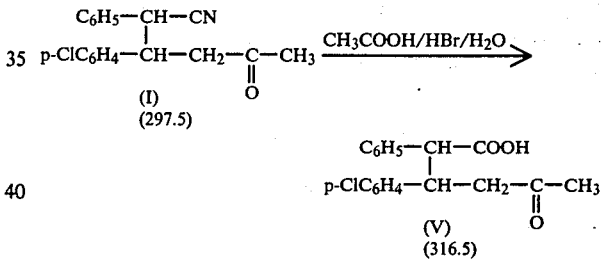

60g (0.2 mole) of the ketonitrile (I) are heated under reflux for 5 hours in 350 cm$^3$ of a water/acetic acid/hydrobromic acid solution obtained from 700 cm$^3$ of acetic acid, 166 cm$^3$ of azeotropic hydrobromic acid and 44 cm$^3$ of water. After cooling, the solution is poured into 1,000 cm$^3$ of ice-cooled water. The acid first separates out in the form of an oil and this oil subsequently crystallizes. The crystals are filtered off and washed with water until the washings are neutral, in order to remove the acetic acid. 52 g of crude product are recovered.

Yield: 82%.
Melting point: 203°-208° C.
This product is recrystallized from absolute alcohol.
Melting point 204°-205° C.
Yield: 80%.

| I.R. (KBr): | ν O—H: 3,500-2,500 cm$^{-1}$, ν C=O: 1,695-1,710 cm$^{-1}$. | | |
|---|---|---|---|
| Analysis: | (C$_{18}$H$_{17}$ClO$_3$) | C | H | Cl |
| | Calculated % | 68.35 | 5.37 | 11.08 |
| | Found % | 68.45 | 5.42 | 11.01 |

NMR carried out on the crude product (VII) shows the presence of two diastereoisomers (with respect to the carbons in the 2- and 3-positions). The determination carried out on the signal of the protons $H_{(6)}$ gives the percentage of each diastereoisomer, namely:
 Erythro: 75%
 Threo: 25%

Recrystallization from absolute ethanol makes it possible to obtain the pure erythro isomer.

| NMR: | |
|---|---|
| (CD$_3$COCD$_3$) + (DMSO)-d$_6$ | δ : 7.30–7.60 ppm, multiplet for 9 aromatic protons. |
| | δ : 3.90 ppm, multiplet for 2 protons $H_{(2)}$ and $H_{(3)}$. |
| 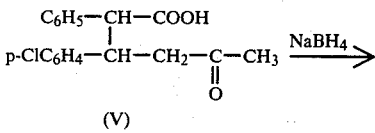 | δ : 2.60 ppm, multiplet for 2 protons $H_{(4)}$. |
| | δ : 1.80 ppm, singlet for 3 protons $CH_{3(6)}$. |

(c) Preparation of erythro-3-(4'-chlorophenyl)-5-hydroxy-2-phenylhexanoic acid

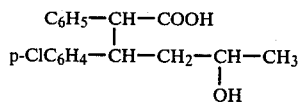

(V)

(316.5)

$$\begin{array}{c} C_6H_5-CH-COOH \\ | \\ p\text{-}ClC_6H_4-CH-CH_2-CH-CH_3 \\ | \\ OH \end{array}$$

(VI)

(318.5)

40g (0.12 mole) of the acid (V) (pure erythro diastereoisomer) are suspended in 400 cm$^3$ of water. 10g of NaBH$_4$ (10 times the theoretical amount) are dissolved in 200 cm$^3$ of water to which 50 cm$^3$ of 2 N sodium hydroxide solution have been added. The solution of NaBH$_4$ is added slowly to the suspension of the acid, at ambient temperature. After the addition, the mixture is stirred for 12 hours. The medium is then acidified with the necessary amount of concentrated hydrochloric acid.

The hydroxyacid formed is extracted with 200, 100, 50 and 60 cm$^3$ of a methylene chloride/ether mixture (50/50). The organic phases collected are washed with sodium bicarbonate and then with water until the washings are neutral. The organic phase is dried over sodium sulfate. After evaporating off the solvents, 32 g of crude product are recovered.

Yield: 80%.

Melting point = 80° C.

The erythro-hydroxacid (VI) cannot be purified by recrystallization because it cyclizes to give the pyrone when its solutions are heated.

| I.R. (KBr): | ν O—H (alcohol): 3,400 cm$^{-1}$; ν OH (acid): 3,500–2,500 cm$^{-1}$. |
|---|---|
| | ν C=O: 1,700 cm$^{-1}$. |
| Mass spectrum: | C$_{18}$H$_{19}$O$_3$Cl (318) |
| Found: | 300, 302 (3:1) M$^+$ −18 |
| | 165, 167 (3:1) p-ClC$_6$H$_4$—CH=CH—CH$^+$—CH$_3$ |
| | 118 (3:1) C$_6$H$_5$—CH—C≡O$^+$ |

(d) Preparation of cis-4-(4'-chlorophenyl)-6-methyl-3-phenyl-3,4,5,6-tetrahydropyrone-2

$$\begin{array}{c} C_6H_5-CH-COOH \\ | \\ p\text{-}ClC_6H_4-CH-CH_2-CH-CH_3 \\ | \\ OH \end{array} \xrightarrow{\text{Acetic anhydride}}$$

(VI)

(318.5)

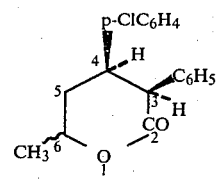

(III)

(300.5)

30g (0.09 mole) of hydroxyacid (VI) are heated under reflux in 150 cm$^3$ of acetic anhydride for one hour.

After distillation of the acetic anhydride under reduced pressure, the residue is taken up in 200 cm$^3$ of chloroform. The mixture is washed with water until the washings are neutral. The organic phase is dried over sodium sulfate. After evaporating off the solvent, 21 g of crude product are recovered.

Yield: 75%.

Melting point = 180°–185° C.

| I.R. (KBr): | ν C=O: 1,725 cm$^{-1}$. |
|---|---|
| Mass spectrum: | C$_{18}$H$_{17}$ClO$_2$: 300 |
| Found: | 300, 302 (3:1) : M$^+$ |
| | 165, 167 (3:1) : p-ClC$_6$H$_4$—CH=CH—CH$^+$—CH$_3$ |
| | 118 : C$_6$H$_5$—CH—C≡O$^+$ |
| NMR: | (CD$_3$COCD$_3$ + DMSO) |
| | δ: 6.7–7.6 ppm, multiplet for 9 aromatic protons. |
| | δ: 4.7 ppm, multiplet for 1 proton $H_{(6)}$. |
| | δ: 4.2 ppm, doublet for 1 proton $H_{(3)}$. $JH_{(3)}$-$H_{(4)}$: 6.5 Hz. |
| | δ: 3.7 ppm, multiplet for 1 proton $H_{(4)}$. |
| | δ: 1.9 ppm, multiplet for 2 protons $H_{(5)}$ in the two isomers. |
| | δ: 1.3 ppm, doublet for 3 protons in —CH$_{3(6)}$ for one diastereoisomer. J CH$_3$—$H_{(6)}$=6Hz. |
| | δ: 1.4 ppm, doublet for 3 protons CH$_{3(6)}$ for the second diastereoisomer. J CH$_3$—$H_{(6)}$= 6 Hz. |

The coupling constant between the protons in the 3- and 4-positions, namely 6.5 Hz, shows that the structure of the pyrone obtained is cis.

Furthermore, the determination of the two diastereoisomers resulting from the reduction of the carbonyl group of the ketoacid (V) gives the percentage of these two diastereoisomers.

α/β: 60:40 (crude product).

Recrystallization from alcohol makes it possible to enrich the pyrone obtained in one isomer. NMR determination then indicates a composition of α/β: 80/20.

Melting point = 182°–185° C.

A second recrystallization from ethanol provides a product having a melting point equal to 186°–190° C.

NMR shows a percentage of α of more than 90%. A third recrystallization is carried out and the product determined at 250 MHz shows a proportion of the α diastereoisomer which is virtually equal to 100%.

EXAMPLE VII

Preparation of 4-(4'-chlorophenyl)-6-methyl-3-phenyl-3,4,5,6-tetrahydropyrone-2 via 3-(4'-chlorophenyl)-5-oxo-2-phenylhexanoic acid (a) Preparation of erythro-2-(4'-chlorophenyl)-4-oxo-1-phenylpentanecarbonitrile The method described in Example I is used for the synthesis of the product I.

NMR shows that the product obtained contains 90% of the erythro isomer and 10% of the threo isomer after recrystallization from absolute ethanol.

Melting point: 130°–132° C.
Yield of the reaction: 90%.
Yield of the recrystallization: 90%.

(b) Preparation of erythro-3-(4'-chlorophenyl)-5-oxo-2-phenylhexanoic acid

The method described in Example VI is used for the preparation of the product (V).

After two recrystallizations from absolute alcohol, NMR only shows the presence of the erythroketoacid.

Melting point=204–205° C.
Yield of the reaction: 80%.
Yield of the recrystallizations: 80%.

(c) Preparation of the sodium salt of erythro-3-(4'-chlorophenyl)-5-oxo-2-phenylhexanoic acid

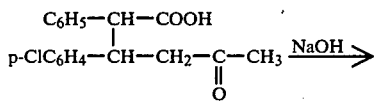

(V)

(316.5)

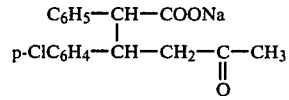

(VIII)

(338.5)

17 g (0.054 mole) of this acid (V) are suspended in 150 cm³ of absolute alcohol. The product is dissolved by heating gently to 40° C. Sodium hydroxide (10% excess) is added slowly. After the addition is complete, the salt formed precipitates. The ethanol is evaporated off and the resulting product is recrystallized from an alcohol/water mixture (80/20). 17 g of product are recovered.

Yield: 90%;
melting point=283° C.

| I.R. (KBr): | $\nu C=O$: 1,705 cm⁻¹; $\nu COO^-$: 1,580 and 1,390 cm⁻¹. |
|---|---|
| NMR (D₂O): | |
| | δ: 7.3 ppm, multiplet for 9 aromatic protons. |
| | δ: 3.65 ppm, multiplet for 2 protons H₍₂₎ and H₍₃₎. |
| | δ: 2.50 ppm, multiplet for 2 protons H₍₄₎. |
| | δ: 1.70 ppm, singlet for 3 protons CH₃₍₆₎. |

This keto-salt is acidified with hydrochloric acid. The corresponding acid obtained is to be used for determining the configuration of the keto-salt formed.

NMR carried out on the acid leads to the assignment of the erythro configuration to the acid and hence to the corresponding salt.

(d) Preparation of cis- and trans-4-(4'-chloro-phenyl)-6-methyl-3-phenyl-3,4,5,6-tetrahydropyrone-2, III

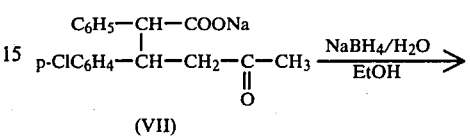

(VII)

(338.5)

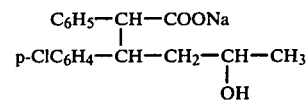

(IV)

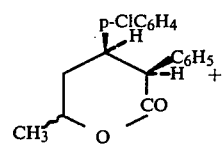 + 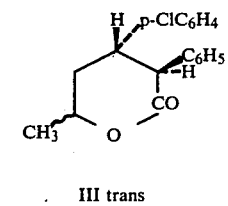

III cis . III trans 10 g (0.03 mole) of keto-salt (VI) are reduced with 1 g of NaBH₄ in 100 cm³ of absolute alcohol. After stirring for 12 hours at ambient temperature, the alcohol is evaporated off.

The pyrone is obtained by heating the crude hydroxy-salt (IV) under reflux, for one hour, with a solution of 5 cm³ of hydrochloric acid in 100 cm³ of water. After cooling, extraction is carried out with chloroform. The organic phase is washed with water until the washings are neutral. After drying over sodium sulfate, the chloroform is evaporated off. 5.3 g of crude product are recovered.

Yield: 60%.

EXAMPLE VIII

Preparation of the Pure Cis-pyron from the erythrio-keto-salt

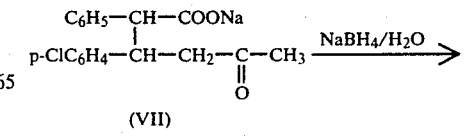

(VII)

ERYTHRO

-continued

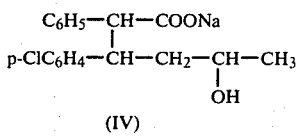

(IV)

NOT ISOLATED

↓ HCl/H₂O

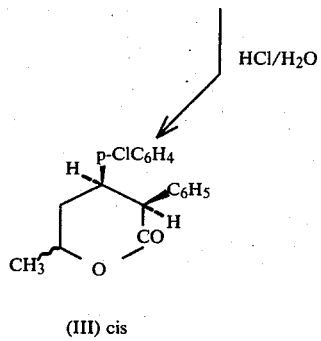

(III) cis 2 g of the keto-salt (VII) are suspended in 20 cm³ of water. 200 mg of NaBH₄, in 5 cm³ of water to which a few drops of 2 N sodium hydroxide solution have been added, are added slowly. The reaction medium is stirred for 12 hours at ambient temperature.

After 12 hours, the mixture is acidified with concentrated hydrochloric acid and heated under reflux for 1 hour. After cooling, the pyrone formed is extracted with chloroform and the chloroform extract is washed with water until the washings are neutral, and dried.

After evaporating off the solvent, 1 g of crude product is recovered.

Yield: 60%.

NMR carried out on the crude product shows the presence exclusively of the cis-pyrone. Thus, if the reduction is carried out in a solely aqueous medium, no epimerization is observed. This clearly shows the epimerizing action of the reduction system, namely NaBH₄/EtOH.

EXAMPLE IX

Preparation of Trans- and Cis-4-(4'-chlorophenyl)-6-methyl-3-phenyl-3,4,5,6-tetrahydropyrone-2, IIIα

(a) Preparation of erythro-3-(4'-chlorophenyl)-5-oxo-2-phenylhexanoic acid ethyl ester

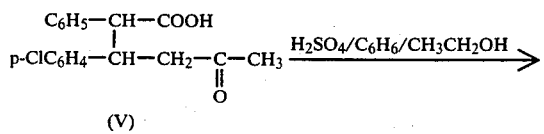

(V)
(316.5)

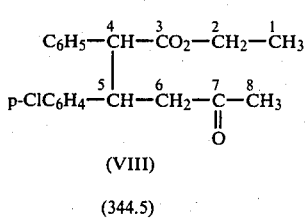

(VIII)
(344.5)

The preparation of the pure erythro isomer of the acid (V), used for the preparation of the ester, is described in Example VI.

10 g (0.03 mole) of acid (V) are heated under reflux for 6 hours in a mixture of benzene (100 cm³) and ethanol (60 cm³), to which 10 cm³ of concentrated sulfuric acid have been added. The water liberated during the esterification is removed from the reaction medium by azeotropic distillation. After cooling, the excess ethanol and the benzene are evaporated off. The residue is taken up in chloroform and the organic phase is washed with bicarbonate and with water until the washings are neutral. The organic phase is dried over sodium sulfate and the solvent is evaporated off. 9 g of product are recovered.

NMR carried out on the crude product containing the ester formed shows the presence of a single diastereoisomer with respect to the carbons in the 4- and 5-positions. Acknowledging that the esterification of the erythro-acid (V) does not cause any epimerization, the ester obtained is therefore exclusively erythro.

Melting point: 95°–97° C.; yield: 90%.
The product is recrystallized from absolute ethanol.
Melting point: 105°–106° C.; yield: 80%.

(b) Preparation of erythro-3-(4'-chlorophenyl)-5-hydroxy-2-phenylhexanoic acid ethyl ester

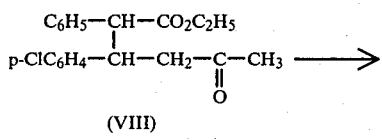

(VIII)
(344.5)

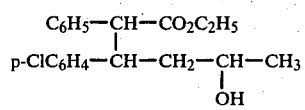

(IX)
(346.5)

10 g of the ketoester (VIII) are suspended in 100 cm³ of absolute ethanol. 1 g of NaBH₄, in 10 cm³ of water to which half a pellet of sodium hydroxide has been added, is added slowly to the suspension of ester. The reaction medium is stirred for 3 hours at 15° C. The ethanol is then evaporated off and the residue is taken up in chloroform. The organic phase is washed with water until the washings are neutral. NMR carried out on the crude product shows the presence of a single diastereoisomer with respect to the carbons in the 4-and 5-positions. The configuration is furthermore determined as being erythro. The two new diastereoisomers with respect to the carbon in the 7-position, resulting from the reduction of the carbonyl, are not visible in NMR, probably because of the free rotation about the carbon-carbon bond. The product is recrystallized from a mixture of carbon tetrachloride and hexane. Melting point=104°–105° C. Yield: 52%.

I.R. (KBr): ν O—H: 3,380 cm$^{-1}$, ν C=O (ester): 1,725 cm$^{-1}$.

NMR (CD$_3$COCD$_3$)

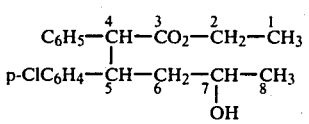

(IX)

| | |
|---|---|
| δ : | 7.40 ppm, multiplet for 9 aromatic protons. |
| δ : | 3.80 ppm, multiplet for 5 protons H$_{(2)}$, H$_{(4)}$, H$_{(5)}$ and H$_{(7)}$. |
| δ : | 3.30 ppm, signal for 1 proton: O—H. |
| δ : | 1.50 ppm, multiplet for 2 protons: H$_{(6)}$. |
| δ : | 0.95 ppm, doublet for 3 protons: CH$_{3(8)}$. J H$_{(8)}$-H$_{(7)}$ = 6.0 Hz. |
| δ : | 0.90 ppm, triplet for 3 protons: CH$_{3(1)}$. J H$_{(1)}$-H$_{(2)}$ = 6.5 Hz. |

Analysis: C$_{20}$H$_{23}$ClO$_3$

| | C% | H% | Cl% |
|---|---|---|---|
| Calculated: | 69.26 | 6.68 | 10.22 |
| Found: | 69.34 | 6.50 | 10.32 |

(c) Preparation of the sodium salt of 3-(4'-chlorophenyl)-5-hydroxy-2-phenylhexanoic acid

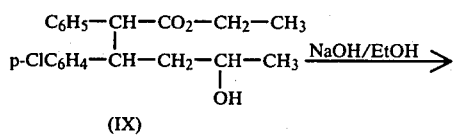

(IX)
(34.5)

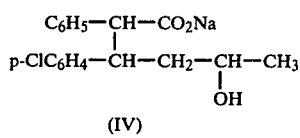

(IV)
(340.5)

5 g of the hydroxyester (IX), as the pure erythro isomer, are dissolved in 50 cm$^3$ of ethanol under the action of heat, and sodium hydroxide (10% excess) in 10 cm$^3$ of water is added slowly. After heating under reflux for 15 hours, the reaction medium is cooled and part of the ethanol is evaporated off. A product crystallizes, it is redissolved under the action of heat and the solution is filtered hot. A yellowish product solidifies. After filtration, it is recrystallized from an alcohol/water mixture (50/50). 2.5 g of recrystallized product are recovered. Yield=50%. Melting point=273°-274° C. The production of the hydroxysalt is verified by I.R.

(d) Preparation of trans-4-(4'-chlorophenyl)-6-methyl-3-phenyl-3,4,5,6-tetrahydropyrone-2, IIIα

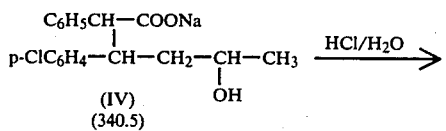

(IV)
(340.5)

trans(IIIα)
(300.5)

The pyrone (IIIα) is obtained by heating the recrystallized hydroxy-salt (IV) under reflux, for one hour, with a solution of 1 cm$^3$ of concentrated hydrochloric acid in 20 cm$^3$ of water. After cooling, the pyrone is extracted with chloroform. The organic phase is washed with bicarbonate and with water until the washings are neutral.

After drying over sodium sulfate, the chloroform is evaporated off. NMR carried out on the crude pyrone shows the presence of a single diastereoisomer with respect to the carbon in the 6-position. By comparison with the results obtained in Example I, it is deduced that this is the pyrone (IIIα).

This method provides the α diastereoisomer directly by means of synthesis and no longer by means of fractional recrystallizations. Yield: 45%; melting point=128°-131° C.

The product obtained is recrystallized from ethanol. Melting point: 136°-137° C.

NMR (CD$_3$COCD$_3$)

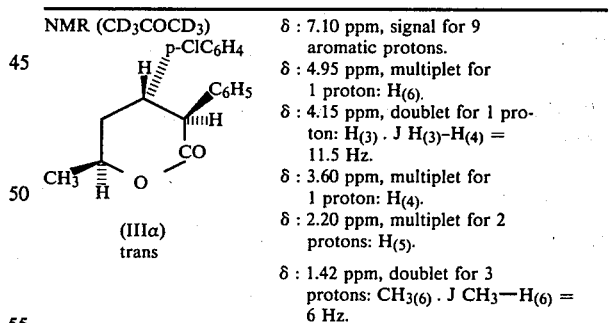

(IIIα)
trans

| | |
|---|---|
| δ : | 7.10 ppm, signal for 9 aromatic protons. |
| δ : | 4.95 ppm, multiplet for 1 proton: H$_{(6)}$. |
| δ : | 4.15 ppm, doublet for 1 proton: H$_{(3)}$. J H$_{(3)}$-H$_{(4)}$ = 11.5 Hz. |
| δ : | 3.60 ppm, multiplet for 1 proton: H$_{(4)}$. |
| δ : | 2.20 ppm, multiplet for 2 protons: H$_{(5)}$. |
| δ : | 1.42 ppm, doublet for 3 protons: CH$_{3(6)}$. J CH$_3$—H$_{(6)}$ = 6 Hz. |

The presence of only one doublet at 4.15 ppm in fact shows the presence of a single diastereoisomer with respect to C$_6$.

(e) Preparation of cis-4-(4'-chlorophenyl)-6-methyl-3-phenyl-3,4,5,6-tetrahydropyrone-2, IIIα

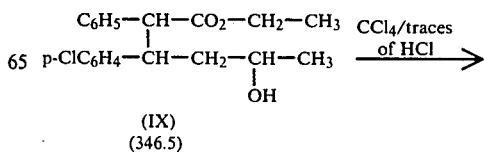

(IX)
(346.5)

-continued

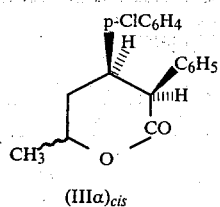

(IIIa)$_{cis}$ 2 g of the hydroxyester (IX) are heated under reflux, for one hour, with 50 cm$^3$ of CCl$_4$ and 1 cm$^3$ of 0.1 N hydrochloric acid. The solution is cooled. A crystalline product forms and is filtered off on a glass frit.

NMR carried out on this product shows the presence of the cis-pyrone which is very rich in one isomer with respect to the carbon in the 6-position. Precise determination indicates that $\alpha/\beta=90/10$ ($\alpha$ and $\beta$ are in fact the two diastereoisomers with respect to the asymmetric carbon C$_6$). Melting point=186°–190° C. Recrystallization is carried out from alcohol. The recrystallized product obtained is determined by NMR at 80 MHz. NMR only shows the presence of a single diastereoisomer to the extent of 100%. Melting point=189°–190° C.

| NMR (80 MHz): | $\delta$ : 7.40 ppm, signal for 5 aromatic protons (phenyl at C$_3$). |
|---|---|
| (CD$_3$COCD$_3$ + DMSO-d$_6$) | $\delta$ : 6.90 ppm, signal for 4 aromatic protons (phenyl at C$_4$). |
| | $\delta$ : 4.90 ppm, multiplet for 1 proton: H$_{(6)}$. |
| | $\delta$ : 4.25 ppm, doublet for 1 proton: H$_{(3)}$. |
| | J H$_{(3)}$–H$_{(4)}$ = 6 Hz. |
| | $\delta$ : 3.50 ppm, multiplet for 1 proton: H$_{(4)}$. |
| | $\delta$ : 2.10 ppm, multiplet for 2 protons: H$_{(5)}$. |
| | $\delta$ : 1.55 ppm, doublet for 3 protons: CH$_{3(6)}$. |
| | J CH$_3$–H$_{(6)}$ = 6 Hz. |

This process therefore makes it possible to obtain the two cis and trans isomeric pyrones from the same product, namely the hydroxyester (IX), and, of much greater importance, to selectively obtain a single diastereoisomer of each pyrone, namely the $\alpha$ diastereoisomer.

ACCOUNT OF PHARMACOLOGICAL EXPERIMENTS CARRIED OUT IN ORDER TO DEMONSTRATE THE THERAPEUTIC PROPERTIES OF THE COMPOUNDS OF THE GENERAL FORMULAE IIIa AND IIIb

The halogen derivatives of a δ-hydroxycarboxylic acid, according to the present invention, possess remarkable therapeutic properties and, in particular, an antidepressive psychostimulant activity, as is apparent from the experiments carried out employing these derivatives.

All the experiments reported below were carried out on male rats having a weight of between 170 and 220 g (Wistar AF strain) and male mice having a weight of between 18 and 23 g (Swiss NMRI strain), unless otherwise stated in the following text.

All the experiments were carried out in a laboratory at a constant temperature (22°±1° C.).

All the experiments were carried out blind (the experimenter being unaware, when carrying out the tests, which animals had received the supposedly active substance and at which dose).

Unless otherwise stated, 10 animals were always used per batch.

Determination of the acute toxicity to mice

Method used: BEHRENS and KARBER

| Substance | LD$_{50}$ (oral administration) | LD$_{50}$ (intraperitoneal administration) |
|---|---|---|
| 4-(4'-Chlorophenyl)-6-methyl-3-phenyl-3,4,5,6-tetrahydropyrone-2 (Example I) | 1,050 mg/kg | 520 mg/kg |
| p-ClC$_6$H$_4$—CH—CH$_2$—CHOH—CH$_3$<br>\|<br>C$_6$H$_5$—CH—CO$_2$Na<br>(product IV obtained in accordance with Examples IX) | 310 mg/kg | 160 mg/kg |

Observation of the animals

In the case of rats as in the case of mice, at doses below the toxic doses, a slight excitation is observed, with an increase in the reactivity to touch or to sound stimuli. This stimulation is not accompanied by motor incoordination or abnormal or stereotyped movements. Moreover, under these conditions, no modification of the diameter of the pupil is observed; however, a discrete hyperthermia is observed. The stereotyped movements are observed from 4 to 8 mg.kg$^{-1}$ for the product obtained in accordance with Example I and from 8 to 32 mg.kg$^{-1}$ for the product IV obtained in accordance with Example IX.

The following are only observed at doses which are very close to the fatal doses: trembling, a very intense hyper-reactivity to stimuli, an inter-aggressiveness and convulsive phenomena with extension of the hind legs. Under these conditions, a hyperthermia of about 1° C. is also observed.

Moreover, an increase in the sexual behaviour was observed in the case of rats.

Motor activity in mice

The motor activity was determined with the aid of activity meters having photoelectric cells (Boissier and Simon, Arch. int. Pharmacodyn. 1965, 158, 212–221). A minimum of 10 animals was always used per batch.

The mice are placed in the activity meter just after the oral or intraperitoneal administration of the product acccording to the invention, obtained in accordance with Example I. The motor activity is measured as from the introduction into the activity meter up to the 60th minute. The counters are read after 30 minutes, then reset to 0 and read every 10 minutes for 30 minutes.

The results obtained are expressed in Tables Ia and Ib below:

TABLE Ia

INFLUENCE OF THE PRODUCT OBTAINED IN ACCORDANCE WITH EXAMPLE I ON THE MOTOR ACTIVITY IN MICE

| Number of mice | mg/kg | Method of administration | \multicolumn{8}{c}{Number of rays passed through by mice at: (minutes)} |||||||||
|---|---|---|---|---|---|---|---|---|---|---|
| | | | 30 | Sd | Test | 30 + 10 | 30 + 20 | 30 + 30 | Sd | Test |
| 40 | 0 | intraperitoneal | 383 | 18 | | 56 | 120 | 181 | 21 | |
| 10 | 1 | intraperitoneal | 400 | 32 | NS | 76 | 163 | 235 | 42 | NS |
| 20 | 2 | intraperitoneal | 474 | 33$^b$ | 2 684 | 114 | 231 | 331 | 33$^c$ | 4 042 |
| 10 | 4 | intraperitoneal | 529 | 17$^c$ | 4 005 | 129 | 269 | 322 | 50$^b$ | 2 951 |
| 10 | 8 | intraperitoneal | 659 | 66$^c$ | 5 827 | 147 | 309 | 467 | 85$^c$ | 4 945 |
| 20 | 16 | intraperitoneal | 763 | 50$^c$ | 8 809 | 176 | 336 | 465 | 56$^c$ | 5 859 |
| 10 | 32 | intraperitoneal | 891 | 77$^c$ | 9 967 | 187 | 422 | 594 | 102 | 6 481 |
| 30 | 0 | oral | 507 | 25 | | 116 | 236 | 321 | 26 | |
| 20 | 4 | oral | 462 | 30 | NS | 139 | 257 | 386 | 37 | NS |
| 20 | 8 | oral | 478 | 32 | NS | 157 | 314 | 461 | 41$^b$ | 3 096 |
| 20 | 16 | oral | 629 | 27$^c$ | 3 298 | 232 | 428 | 636 | 31$^c$ | 7 902 |
| 10 | 32 | oral | 783 | 72$^c$ | 4 660 | 270 | 587 | 869 | 62 | 9 377 |

$^a$difference significant at the 0.05 level
$^b$difference significant at the 0.01 level
$^c$difference significant at the 0.001 level
Sd = standard deviation
NS = not significant

TABLE Ib

INFLUENCE OF THE PRODUCT OBTAINED IN ACCORDANCE WITH EXAMPLE I ON THE MOTOR ACTIVITY IN MICE

| Number of mice | mg/kg | Method of administration | \multicolumn{8}{c}{Number of rays passed through by mice at: (minutes)} |||||||||
|---|---|---|---|---|---|---|---|---|---|---|
| | | | 30 | Sd | Test | 0 + 10 | 30 + 20 | 30 + 30 | Sd | Test |
| 10 | 0 | | 476 | 29 | | 105 | 206 | 271 | 39 | |
| 10 | 2 | | 417 | 28 | | 119 | 221 | 334 | 40 | |
| 10 | 4 | | 472 | 27 | | 129 | 259 | 376 | 43 | NS |
| 10 | 8 | | 452 | 37 | | 141 | 286 | 443 | 48 | 2,770$^b$ |
| 10 | 16 | | 565 | 35 | NS | 172 | 359 | 537 | 47 | 4,35$^c$ |
| 10 | 32 | | 560 | 35 | NS | 184 | 376 | 547 | 60 | 3,830$^c$ |

$^b$difference significant at the 0.01 level
$^c$difference significant at the 0.001 level
Ns = not significant Study of the stereotypies in rats The tests were carried out on batches of 6 rats for each dose; immediately after the oral or intraperitoneal administration, the animals are placed in individual, transparent plastic 20×10×10 cm boxes provided with a pierced stainless steel lid. The stereotyped movements are rated from 0 to 3, in accordance with the method described by Simon and Chermat (J. Pharmacol. (Paris), 1972, 3, 235–238) every 10 minutes until they disappear in all the animals. The detailed curves are plotted and the surface area of the curve is calculated as described in the above reference.

The results, expressed as the mean surface area of the curve, are indicated in the attached figure. They show the presence of very significant stereotypies from 8 mg.kg$^{-1}$. As indicated by the figure, the activity of the product obtained in accordance with Example II is slightly greater on oral administration.

Anti-reserpine activity in mice

At time 0, the mice receive reserpine (2.5 mg.kg$^{-1}$) by intraperitoneal administration.

After 4 hours, when the hypothermia is significant (30 to 31°C.), the substance to be studied is administered intraperitoneally or orally. The rectal temperature is measured, using a probe, carrying a thermoelectric couple, inserted to a constant depth, every 30 minutes for 2 hours.

The detailed results are indicated in Tables IIa and IIb below:

TABLE IIa

ANTI-RESERPINE ACTIVITY OF THE PRODUCT OBTAINED IN ACCORDANCE WITH EXAMPLE I

| Number of mice | mg/kg | Method of administration | Rectal temperatures °C. ± SD at : (minutes) ||||
|---|---|---|---|---|---|---|
| | | | 30 | 60 | 90 | 120 |
| 24 | 0 | intraperitoneal | 31.1 ± 0.30 | 30.7 ± 0.36 | 30.6 ± 0.37 | 30.3 ± 0.39 |
| 6 | 4 | intraperitoneal | 32.7 ± 0.56$^a$ | 33.7 ± 0.47$^c$ | 33.1 ± 0.39$^b$ | 32.2 ± 0.46$^a$ |
| 6 | 8 | intraperitoneal | 33.1 ± 0.32$^b$ | 34.1 ± 0.24$^c$ | 34.0 ± 0.38$^c$ | 33.6 ± 0.49$^c$ |
| 6 | 16 | intraperitoneal | 35.3 ± 0.51$^c$ | 35.7 ± 0.34$^c$ | 35.3 ± 0.37$^c$ | 35.0 ± 0.44$^c$ |
| 6 | 32 | intraperitoneal | 34.8 ± 0.48$^c$ | 36.2 ± 0.38$^c$ | 35.6 ± 0.38$^c$ | 35.7 ± 0.37$^c$ |
| 6 | 4 | oral | 30.6 ± 0.39 | 30.6 ± 0.45 | 30.7 ± 0.59 | 30.4 ± 0.67 |
| 12 | 8 | oral | 31.1 ± 0.36 | 31.4 ± 0.56 | 31.5 ± 0.57 | 31.3 ± 0.56 |
| 6 | 16 | oral | 31.4 ± 0.41 | 32.6 ± 0.56$^a$ | 32.8 ± 0.53$^b$ | 32.8 ± 0.45$^b$ |
| 12 | 32 | oral | 31.4 ± 0.31 | 32.6 ± 0.44$^c$ | 32.9 ± 0.41$^c$ | 32.8 ± 0.38$^c$ |
| 6 | 64 | oral | 33.8 ± 0.58$^c$ | 34.5 ± 0.33$^c$ | 34.4 ± 0.39$^c$ | 34.4 ± 0.35$^c$ |
| 6 | 128 | oral | 33.1 ± 0.56$^b$ | 34.1 ± 0.56$^c$ | 34.3 ± 0.58$^c$ | 34.2 ± 0.53$^c$ |

TABLE IIa-continued
ANTI-RESERPINE ACTIVITY OF THE PRODUCT OBTAINED IN ACCORDANCE WITH EXAMPLE I

| Number of mice | mg/kg | Method of administration | Rectal temperatures °C. ± SD at : (minutes) | | | |
|---|---|---|---|---|---|---|
| | | | 30 | 60 | 90 | 120 |
| 6 | 256 | oral | 33.5 ± 0.47[c] | 35.2 ± 0.15[c] | 35.3 ± 0.34[c] | 35.1 ± 0.33[c] |

[a]difference significant to the 0.05 level
[b]difference significant at the 0.01 level
[c]difference significant to the 0.001 level

TABLE IIb
ANTI-RESERPINE ACTIVITY OF THE PRODUCT IV OBTAINED IN ACCORDANCE WITH EXAMPLE IX

| Number of mice | mg/kg | Method of administration | Rectal temperatures °C. ± SD at: (minutes) | | | |
|---|---|---|---|---|---|---|
| | | | 30 | 60 | 90 | 120 |
| 6 | 0 | oral | 30.6 ± 0.39 | 30.6 ± 0.45 | 30.7 ± 0.59 | 30.4 ± 0.67 |
| 6 | 8 | oral | 30.9 ± 0.36 | 32.0 ± 0.56 | 32.2 ± 0.57 | 33.2 ± 0.56 |
| 6 | 16 | oral | 31.1 ± 0.39 | 32.5 ± 0.60[a] | 32.7 ± 0.51[b] | 33.1 ± 0.43[b] |
| 6 | 32 | oral | 31.3 ± 0.31 | 33.0 ± 0.44[c] | 33.7 ± 0.41[c] | 33.2 ± 0.38[c] |
| 6 | 64 | oral | 32.8 ± 0.40[c] | 34.3 ± 0.32[c] | 34.5 ± 0.38[c] | 34.4 ± 0.41[c] |

[a]difference significant at the 0.05 level
[b]difference significant at the 0.01 level
[c]difference significant at the 0.001 level It is apparent from the results summarized in Tables IIa and IIb that the antagonistic effect exerted by the medicaments according to the invention is very marked on the experimental model used.

Anti-apomorphine activity in mice

At time 0, the mice receive, by oral administration, the product obtained in accordance with Example I; after 30 minutes, they receive apomorphine by subcutaneous administration, either at a dose of 1 mg.kg$^{-1}$ or at a dose of 16 mg.kg$^{-1}$. They are then placed in individual boxes (11×3.5×4 cm) which enable them to be observed. The rectal tamperature is measured 30 minutes after the administration of apomorphine. Control animals receive distilled water in place of the product, according to the invention, obtained in accordance with Example II. The average hypothermia observed in these control animals was 34.9° C. for the animals which had received apomorphine at a dose of 1 mg.kg$^{-1}$ and 33.5° C. for the animals which had received apomorphine at a dose of 16 mg.kg$^{-1}$. For each dose of medicament according to the invention, the percentage inhibition of the hypothermia was calculated. The results are expressed in Table III below. They show that the medicament according to the invention exerts a more marked antagonism with respect to the effects of a strong dose of apomorphine than with respect to the effects of a weak dose.

At sufficient doses of medicament according to the invention, the hypothermia induced by apomorphine is antagonised in a virtually complete manner. On the other hand, the stereotyped movements and the climbing caused by apomorphine were not modified in the animals which had received the medicament according to the invention, regardless of the dose.

TABLE III
INFLUENCE OF THE MEDICAMENTS ACCORDING TO THE INVENTION ON THE HYPOTHERMIA CAUSED BY APOMORPHINE

| Number of mice | mg/kg | Method of administration | Rectal temperatures Results in % inhibition of the hypothermia | |
|---|---|---|---|---|
| | | | Apomorphine 1 mg . kg$^{-1}$, administered subcutaneously | Apomorphine 16 mg . kg$^{-1}$, administered subcutaneously |
| 6 | 0.5 | intra-peritoneal | 7 | −5 |
| 12 | 2 | intra-peritoneal | 3 | 45 |
| 6 | 4 | intra-peritoneal | −13 | 39 |
| 6 | 16 | intra-peritoneal | 10 | 51 |
| 12 | 4 | oral | 0 | 31 |
| 12 | 8 | oral | −2 | 40 |
| 12 | 16 | oral | 0.5 | 42 |
| 12 | 32 | oral | 45 | 77 |
| 6 | 64 | oral | 51 | 86 |
| 6 | 128 | oral | 68 | 81 |
| 6 | 256 | oral | 89 | 116 |

Anti-oxotremorine activity in mice

At time 0, the mice receive oxotremorine (0.5 mg.kg$^{-1}$) by intraperitoneal administration; after 30 minutes, either distilled water or the medicament according to the invention, obtained in accordance with Example I, is administered to the mice intraperitoneally or orally.

The mice are then observed and the trembling is rated from 0 to 3 as a function of its intensity, every 10 minutes for 30 minutes. Moreover, the existence of peripheral symptoms (tears, hypersialosis and defections) is observed for 2 hours, in the presence or absence of trembling. The rectal temperature is measured every 30 minutes for 2 hours, after administration of oxotremorine.

The results relating to the temperature are indicated in Table IV below. They show a marked antagonism. On the other hand, the medicament according to the invention, obtained in accordance with Example II, at the doses studied using oral or intraperitoneal administration, did not cause any modification of the trembling and of the peripheral symptoms caused by oxotremorine.

TABLE IV

INFLUENCE OF THE MEDICAMENT ACCORDING TO THE INVENTION ON THE HYPOTHERMIA INDUCED BY OXOTREMORINE IN MICE

| Number of mice | mg/kg | Method of administration | Rectal temperatures °C. at: (minutes) | | | |
|---|---|---|---|---|---|---|
| | | | 30 | 60 | 90 | 120 |
| 36 | 0 | | 30.1 ± 0.20 | 28.7 ± 0.24 | 28.4 ± 0.30 | 29.5 ± 0.55 |
| 6 | 2 | intraperitoneal | 30.8 ± 0.43 | 29.1 ± 0.46 | 29.4 ± 0.52 | 29.9 ± 0.77 |
| 6 | 4 | intraperitoneal | 30.2 ± 0.36$^c$ | 31.8 ± 0.42$^c$ | 33.5 ± 0.49$^c$ | 35.7 ± 0.40$^c$ |
| 6 | 8 | intraperitoneal | 32.1 ± 0.52$^c$ | 31.3 ± 0.52$^c$ | 32.2 ± 0.61$^c$ | 33.8 ± 0.91$^c$ |
| 12 | 16 | intraperitoneal | 32.9 ± 0.46$^c$ | 32.0 ± 0.65$^c$ | 32.8 ± 0.60$^c$ | 35.9 ± 0.81$^c$ |
| 6 | 32 | intraperitoneal | 32.0 ± 0.70$^c$ | 31.2 ± 0.73$^c$ | 32.2 ± 0.85$^c$ | 33.2 ± 1.2$^b$ |
| 6 | 64 | intraperitoneal | 34.0 ± 0.87$^c$ | 33.0 ± 1.2$^c$ | 33.7 ± 1.15$^c$ | 34.5 ± 1.0$^c$ |
| 6 | 1 | oral | 29.8 ± 0.40 | 27.8 ± 0.65 | 27.8 ± 1.36 | 28.0 ± 1.65 |
| 6 | 2 | oral | 31.5 ± 0.43$^b$ | 31.0 ± 0.71$^c$ | 31.2 ± 0.86$^c$ | 31.9 ± 1.14 |
| 12 | 4 | oral | 31.8 ± 0.38$^c$ | 31.0 ± 0.34$^c$ | 31.6 ± 0.91$^c$ | 32.4 ± 0.89$^b$ |
| 12 | 8 | oral | 32.6 ± 0.32$^c$ | 32.4 ± 0.29$^c$ | 32.9 ± 0.38$^c$ | 33.8 ± 0.56$^c$ |
| 12 | 16 | oral | 31.9 ± 0.53$^c$ | 31.9 ± 0.49$^c$ | 32.8 ± 0.70$^c$ | 33.6 ± 0.97$^c$ |
| 12 | 32 | oral | 33.0 ± 0.60$^c$ | 32.7 ± 0.63$^c$ | 32.8 ± 0.62$^c$ | 33.7 ± 0.95$^c$ |
| 12 | 64 | oral | 32.2 ± 0.32$^c$ | 31.7 ± 0.52$^c$ | 32.8 ± 0.73$^c$ | 34.1 ± 0.62$^c$ |
| 6 | 128 | oral | 34.8 ± 0.80$^c$ | 34.9 ± 0.59$^c$ | 36.2 ± 0.82$^c$ | 37.1 ± 0.77$^c$ |
| 6 | 256 | oral | 32.4 ± 0.63$^c$ | 31.3 ± 0.73$^c$ | 32.4 ± 1.07$^c$ | 33.9 ± 1.30$^b$ |

$^b$difference significant at the 0.01 level
$^c$difference significant at the 0.001 level Action on the toxicity of yohimbine to mice At time 0, the mice receive, by oral administration, either distilled water or the medicament according to the invention; after 30 minutes, yohimbine hydrochloride (25 mg.kg$^{-1}$) is administered subcutaneously to the mice. The mortality is followed every hour for 4 hours and then recorded after 24 hours.

The results indicated in Tables Va and Vb below show a potentiation of the toxicity of yohimbine by the medicaments according to the invention, which potentiation is marked from a dose of 16 mg.kg$^{-1}$. There is no difference between the figures found after 4 hours and after 24 hours.

TABLE Va

INFLUENCE OF THE MEDICAMENT ACCORDING TO THE INVENTION, OBTAINED IN ACCORDANCE WITH EXAMPLE II, ON THE TOXICITY OF YOHIMBINE IN MICE

| Number of mice | mg/kg | Mortality in % 4 and 24 hours after the administration of yohimbine | |
|---|---|---|---|
| | | 4 | 24 |
| 30 | 0 | 0 | 0 |
| 20 | 2 | 0 | 0 |
| 10 | 4 | 0 | 0 |
| 20 | 8 | 10 | 10 |
| 20 | 16 | 20 | 20 |
| 20 | 32 | 25 | 25 |
| 20 | 64 | 30 | 30 |
| 10 | 128 | 60 | 60 |
| 10 | 256 | 70 | 70 |

TABLE Vb

INFLUENCE OF THE MEDICAMENT ACCORDING TO THE INVENTION OBTAINED IN ACCORDANCE WITH EXAMPLE IV (PRODUCT IV), ON THE TOXICITY OF YOHIMBINE IN MICE (10 mice per dose)

| mg/kg administered orally | Mortality in % 4 and 24 hours after the administration of yohimbine | |
|---|---|---|
| | 4 | 24 |
| 0 | 0 | 0 |
| 2 | 10 | 10 |
| 4 | 20 | 20 |
| 8 | 30 | 30 |
| 16 | 70 | 70 |
| 32 | 80 | 80 |
| 64 | 100 | 100 |
| 128 | 80 | 80 |
| 256 | 100 | 100 |

Interaction with barbital sodium

At time 0, the mice receive, by intraperitoneal or oral administration, distilled water or the medicament according to the invention. After 30 minutes, they receive barbital sodium (180 mg.kg$^{-1}$) by intraperitoneal administration. The times for the suppression and reappearance of the climbing reflex were noted for each animal.

The results obtained are indicated in Table VI below:

TABLE VI

INFLUENCE OF THE MEDICAMENT ACCORDING TO THE INVENTION, OBTAINED IN ACCORDANCE WITH EXAMPLE I, ON THE SLEEP INDUCED BY BARBITAL SODIUM (180 mg . kg$^{-1}$) IN MICE

| Number of mice | mg/kg | Method of administration | % of mice which have slept | Time in minutes | |
|---|---|---|---|---|---|
| | | | | for induction of sleep | of sleep |
| 6 | 0 | intraperitoneal | 100 | 21 | 88 ± 8 |
| 6 | 2 | intraperitoneal | 100 | 27 | 67 ± 16 |
| 6 | 4 | intraperitoneal | 83 | 22 | 37 ± 13 |

TABLE VI-continued
INFLUENCE OF THE MEDICAMENT ACCORDING TO THE INVENTION, OBTAINED IN ACCORDANCE WITH EXAMPLE I, ON THE SLEEP INDUCED BY BARBITAL SODIUM (180 mg . $kg^{-1}$) IN MICE

| Number of mice | mg/kg | Method of administration | % of mice which have slept | Time in minutes for induction of sleep | of sleep |
|---|---|---|---|---|---|
| 6 | 8 | intraperitoneal | 83 | 30 | 25 ± 4 |
| 6 | 16 | intraperitoneal | 33 | 38 | 14 |
| 6 | 32 | intraperitoneal | 0 | 0 | 0 |
| 12 | 0 | oral | 100 | 29 | 64 ± 9 |
| 6 | 2 | oral | 83 | 25 | 47 ± 15 |
| 12 | 4 | oral | 25 | 33 | 56 |
| 12 | 8 | oral | 42 | 32 | 43 |
| 6 | 16 | oral | 0 | 0 | 0 |
| 6 | 32 | oral | 00 | 0 | 0 |

The medicament according to the invention, administered orally or intraperitoneally, markedly antagonizes the sleep caused by barbital.

"Anti-fatigue" action in rats

The technique described by Boissier and Simon (Thérapie 1968, 23, 1,267-1,276) was used on rats which were placed in a shuttling-box with two compartments, and had been fatigued beforehand. The medicament according to the invention was administered orally to 6 rats and intraperitoneally to 6 others. Under these conditions, a resumption of the conditioned activity was observed in all the animals, which resumption was statistically significant and lasted an average of 2 hours.

Other tests were carried out they showed an absence of effects of the medicaments according to the invention. They are important insofar as they make it possible to determine the effectiveness profile of these substances and to compare it with that of other known antidepressive psychotropic substances. They are also important because they make it possible to show the absence of modification of a certain number of normal behaviours.

(a) Absence of perturbation of an avoidance conditioning

A simple test for conditioned inhibition was used, namely the four plate test (Aron et al., Neuropharmacology, 1971, 10, 459-470). At doses of 8 and 32 mg.$kg^{-1}$ (10 animals per batch), no modification of the conditioned inhibition in mice was observed. On the other hand, a slight increase in the performance of the animals was observed in this test, but this performance seems to have been related to the stimulant action which was pointed out above.

(b) Absence of modification of the effects of pentobarbital

At time 0, the mice receive, by intraperitoneal or oral administration, distilled water or the medicament according to the invention, obtained in accordance with Example I. After 30 minutes, they receive pentobarbital (50 mg.$kg^{-1}$) by intraperitoneal administration. The times for the suppression and reappearance of the climbing reflex were noted for each animal.

The results are indicated in Table VII below:

TABLE VII
INFLUENCE OF THE MEDICAMENT ACCORDING TO THE INVENTION OBTAINED IN ACCORDANCE WITH EXAMPLE I, ON THE SLEEP INDUCED BY PENTOBARBITOL (50 mg . $kg^{-1}$, administered intraperitoneally) IN MICE

| Number of mice | mg/kg | Method of administration | % of mice which have slept | Time in minutes for induction of sleep | of sleep |
|---|---|---|---|---|---|
| 30 | 0 | intraperitoneal | 100 | 4 | 48 ± 4 |
| 6 | 2 | intraperitoneal | 100 | 4 | 47 ± 7 |
| 6 | 4 | intraperitoneal | 100 | 4 | 55 ± 8 |
| 12 | 8 | intraperitoneal | 100 | 4 | 36 ± 3 |
| 6 | 16 | intraperitoneal | 83 | 4.5 | 26 ± 7 |
| 12 | 32 | intraperitoneal | 92 | 4.5 | 27 ± 3 |
| 6 | 64 | intraperitoneal | 100 | 4 | 30 ± 9 |
| 6 | 128 | intraperitoneal | 83 | 6 | 25 ± 5 |
| 30 | 0 | oral | 100 | 4 | 48 ± 4 |
| 6 | 2 | oral | 100 | 4 | 60 ± 8 |
| 6 | 4 | oral | 100 | 4 | 45 ± 4 |
| 6 | 8 | oral | 100 | 4 | 57 ± 10 |
| 6 | 16 | oral | 100 | 4 | 41 ± 7 |
| 6 | 32 | oral | 100 | 4 | 49 ± 4 |
| 6 | 64 | oral | 100 | 5 | 29 ± 8 |
| 6 | 128 | oral | 100 | 4 | 38 ± 7 |

Up to a dose of 128 mg.$kg^{-1}$, administered intraperitoneally or orally, the medicament according to the invention does not cause any marked antagonism with respect to the hypnotic effect of pentobarbital.

(c) Absence of inhibitory effect of monoamine oxidase

It was verified that, at doses of 16 and 64 mg.$kg^{-1}$, administered orally, the medicament according to the invention did not cause any potentiation of the effects of an infraconvulsive dose of tryptamine (3 mg.$kg^{-1}$, administered intravenously) in rats.

Research into the antagonistic effects of the stereotypies caused in rats by the medicament according to the invention (a) Influence of pimozide At time 0, pimozide (1 mg.$kg^{-1}$) or distilled water is administered intraperitoneally; after 30 minutes, all the animals receive, by intraperitoneal administration, the medicament according to the invention, obtained in accordance with Example III (8 mg.$kg^{-1}$). The stereotypies are assessed as described above. The surface area of the curve of the stereotypies is calculated. This gives:

surface area of the curve of the medicament by itself . . . 63 surface area of the curve of the medicament administered after pimozide . . . 17

Under these experimental conditions, pimozide very significantly antagonizes the stereotypies caused by the medicament according to the invention.

(b) Influence of alpha-methyltyrosine

At time 0, the animals receive, by intraperitoneal administration, either distilled water or alphamethyltyrosine at a dose of 64 mg.$kg^{-1}$; after 150 minutes, they receive, by intraperitoneal administration, the medicament according to the invention, obtained in accordance with Example III, at a dose of 8 mg.kg$^{-1}$.

The animals are observed under the conditions described above in the study of the stereotypies in rats.

Under these experimental conditions, the stereotypies caused by the medicament according to the invention are virtually unmodified under the influence of a pretreatment with alpha-methyltyrosine (surface area of the curve of the medicament by itself: 63; medicament+alpha-methyltyrosine: 60.8).

COMPARISON OF THE ACTIVITIES OF THE ISOMERS

A few experiments were carried out in order to compare the effects of the trans isomer containing:

(a) 100 % of the α diastereoisomer
(b) 100 % of the β diastereoisomer
(c) a mixture (80/20) of these two diastereoisomers.

The acute toxicities of the 3 compounds are similar, the LD$_{50}$, on oral administration to mice, being between 800 and 1,200 mg/kg.

The comparison of the activities was carried out at equivalent doses (32 mg/kg), administered orally to rats or mice. It involves the measurement of the acute toxicities and the tests making it possible to detect the psychoanaleptic effects (motor activity in mice and stereotyped movements in rats) and then the tests making it possible to detect the antidepressive effects (interaction with reserpine and apomorphine).

The results of the tests are slightly dissociated and can be represented schematically as in Table VII below:

TABLE VII

| Isomer 32 mg/kg (administered orally | Increase in the motor activity in mice | Stereo-typy-forming action on rats | Anti-reserpine action | Anti-apomorphine action |
|---|---|---|---|---|
| 100% of α | + | 0 | ± | ++ |
| 100% of β | +++ | +++ | +++ | +++ |
| 80% of α and 20% of β | ++ | ++ | +++ | +++ |

The α diastereoisomer therefore seems to be very different from the β diastereoisomer: the anti-apomorphine activity persists, whereas the anti-reserpine action and the increase in the motor activity in mice are less significant and the stereotype-forming action on rats virtually disappears.

Compared with the mixture of 80 % of α and 20 % of β, the β diastereoisomer seems to be more active and, in particular, to have a greater stimulant action.

CONCLUSION

The effects of the medicaments according to the invention can be represented as follows:

1. Marked stimulant action, characterized by an increase in the motor activity, the presence of stereotypies, anti-fatigue action, and anti-sleep action with respect to barbital but not with respect to pentobarbital. This stimulant action is antagonized by an agent for blocking dopaminergic receptors, namely pimozide, but is not modified by an inhibitor of the synthesis of catecholamines, namely alpha-methyltyrosine. This action therefore appears to differ from that of the substances of the amphetamine group in two characteristics, namely the absence of antagonism towards the hypnotic effects of pentobarbital and the absence of suppression under the influence of alpha-methyltyrosine.

2. Activity of the antidepressive type

The medicaments according to the invention possess effects, in the tests, which are considered as representative of an antidepressive activity, namely anti-reserpine action, antagonistic action towards the hypothermia caused by apomorphine (and, as do the imipramines, the medicament according to the invention provides better opposition to the effects of a strong dose of apomorphine than to those of a weak dose), antagonistic action towards the hypothermia caused by oxotremorine, and potentiation of the toxicity of yohimbine to mice.

3. Absence of inhibitory action on monoamine oxidase (tryptamine test).

4. Absence of peripheral anti-cholinergic effects: no modification of the peripheral symptoms caused by oxotremorine in mice.

The results of the experiments make it possible to class the medicaments according to the invention unequivocally as psychotropic substances having an antidepressive action. They also possess a marked psychostimulant action which differs in its mechanism from that of the noo-analeptic agents or amphetamines. The absence of an inhibitory effect on monoamine oxidase and of a peripheral anti-cholinergic action clearly differentiates them from the two known large groups of antidepressants, namely imipramines and monoamine oxidase inhibitors.

The medicaments according to the present invention, of the general formula IIIa or IIIb, can be used by any methods of administration, at adult doses of between 10 and 500 mg/day.

The foregoing description shows that, regardless of the methods of implementation, the embodiments and the methods of administration adopted, medicaments are obtained having an antidepressive and psychostimulant action which should permit a wide therapeutic use and, in particular:

in all cases: activity towards all depressive states, whether of endogenous origin or of reaction origin, regardless of the age;

in children, difficulties of intellectual fixation, apathy, asthenia, overwork, memory disorders and difficulties of fixation of the attention; and in adults and elderly people: asthenia, reduction in the intellectual activity, apathy, correction of the states of sedation caused by the administration of anti-epileptic medicaments, tranquillizers, neuroleptic agents or the like, and apathy caused by Parkinson's disease.

Thus, as is apparent from the foregoing text, the invention is in no way limited to those methods of implementation, embodiments and methods of administration which have now been described more explicitly; on the contrary, it includes all the variants which can occur to those skilled in the art, without departing from the nature or the scope of the present invention.

We claim:

1. A compound of the formula

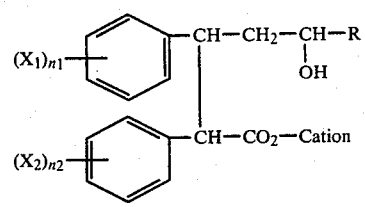

wherein $X_1$ and $X_2$ are chlorine atoms, $n_1$ and $n_2$ are integers between 0 and 5, but, if $n_1=0$, $n_2$ is different from 0, and vice versa, R is hydrogen, alkyl or aryl and Cation represents a pharmaceutically acceptable cation.

2. A compound of the formula

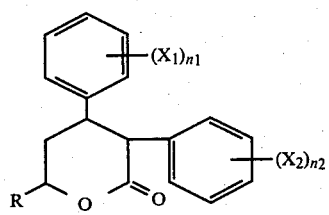

wherein $X_1$ and $X_2$ are chlorine atoms, $n_1$ and $n_2$ are integers between 0 and 5, but, if $n_1=0$, $n_2$ is different from 0, and vice versa, and R is hydrogen, aklyl or aryl.

3. A compound as claimed in claim 2, of the formula

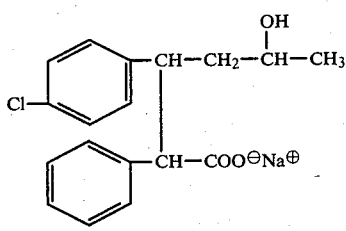

4. A compound as claimed in claim 1 of the formula

5. A compound as claimed in any of claims 1, 2, 3, and 4 which is a pure diastereoisomer.

6. A medicinal composition for treating depressions comprising an antidepressively effective amount of a dose between 10 and 500 mg/day of a compound as claimed in any of claims 1, 2, 3, 4, and 5.

* * * * *

UNITED STATES PATENT AND TRADEMARK OFFICE
CERTIFICATE OF CORRECTION

PATENT NO. : 4,287,206
DATED : Sep. 1, 1981
INVENTOR(S) : Pierre Simon and Jacques Dreux It is certified that error appears in the above—identified patent and that said Letters Patent is hereby corrected as shown below:

In the title:

Item [54], line 2, change "8-HYDROXYCARBOXYLIC" to

--δ-HYDROXYCARBOXYLIC--, and

Item [30], after "Sep. 5, 1978 .............. 78 25457", include --June 21, 1979 [FR] France .......... 79 15888--.

In the abstract:

Item [57], line 1, change "8-hydroxycarboxylic" to

--δ-hydroxycarboxylic--.

Signed and Sealed this

Twenty-third Day of February 1982

[SEAL]

Attest:

Attesting Officer

GERALD J. MOSSINGHOFF

Commissioner of Patents and Trademarks